(12) United States Patent
Link et al.

(10) Patent No.: US 7,318,903 B2
(45) Date of Patent: Jan. 15, 2008

(54) PHOTONIC SENSOR PARTICLES AND FABRICATION METHODS

(75) Inventors: Jamie R. Link, La Jolla, CA (US); Michael J. Sailor, La Jolla, CA (US)

(73) Assignee: The Regents of the University of California, Oakland, CA (US)

(*) Notice: Subject to any disclaimer, the term of this patent is extended or adjusted under 35 U.S.C. 154(b) by 83 days.

(21) Appl. No.: 10/567,917

(22) PCT Filed: Aug. 13, 2004

(86) PCT No.: PCT/US2004/026572

§ 371 (c)(1),
(2), (4) Date: Feb. 6, 2006

(87) PCT Pub. No.: WO2005/034725

PCT Pub. Date: Apr. 21, 2005

(65) Prior Publication Data

US 2006/0255008 A1  Nov. 16, 2006

Related U.S. Application Data

(60) Provisional application No. 60/495,436, filed on Aug. 14, 2003.

(51) Int. Cl.
*C23F 1/00* (2006.01)
*B32B 3/00* (2006.01)

(52) U.S. Cl. ........................ 216/2; 428/312.6

(58) Field of Classification Search ............ 216/2; 428/312.6
See application file for complete search history.

(56) References Cited

U.S. PATENT DOCUMENTS 6,130,748 A * 10/2000 Kruger et al. ............. 356/450
6,521,136 B1    2/2003 Sfez et al.
6,786,968 B2 *  9/2004 Theil ............................. 117/93
6,897,965 B2 *  5/2005 Ghadiri et al. ............. 356/519
7,022,303 B2 *  4/2006 Riman et al. ............ 423/594.9
2002/0191884 A1 12/2002 Letant et al.
2003/0146109 A1  8/2003 Sailor et al.
2005/0009374 A1  1/2005 Gao et al.
2005/0042764 A1  2/2005 Sailor et al.
2006/0051872 A1  3/2006 Sailor et al.

OTHER PUBLICATIONS

Y. Xia, J.A. Rogers, K.E. Paul, G. Whitesides, "Unconventional Methods for Fabricating and Patterning Nanostructures", Chem. Rev., 1999, vol. 99, pp. 1823-1848.

(Continued)

*Primary Examiner*—Roberts Culbert
(74) *Attorney, Agent, or Firm*—Greer, Burns & Crain, Ltd (57) ABSTRACT

The invention is related to optical particles (10), use of optical particles in sensing applications, and methods of fabricating optical particles that can target a desired analyte. The invention is also related to the self assembly of individual optical particles. An advantage of the invention is that it includes self-assembling individual photonic crystal sensors onto a target. In an embodiment of the invention, a processed sensor structure having two generally opposing surfaces is provided, wherein each of the opposing surfaces have different surface affinities, with a first optical structure formed on one of the opposing surfaces, and a second optical structure formed on the other of the opposing surfaces. The chemically and optically asymmetric opposing surfaces will spontaneously align at an organic liquid/water interface. Changes in the optical response of at least one of the opposing surfaces indicate the presence of a particular analyte for sensing applications.

23 Claims, 4 Drawing Sheets

OTHER PUBLICATIONS

M.D. Porter, T.B. Bright, D.L. Allara, C.D. Chidsey, Spontaneously Organized Molecular Assemblies, 4. Structural Characterization of n-Alkyl Thiol Monolayers on Gold by Optical Ellipsometry, Infrared Spectroscopy and Electrochemistry, J. Am. Chem. Soc., 1987, vol. 109, p. 3559-3568.

So-Jung Park, A.A. Lazarides, C.A. Mirkin, R.L. Letsinger, "Directed Assembly of Periodic Materials from Protein and Oligonucleotide-Modified Nanoparticle Building Blocks," Angew. Chem. Int. Ed. 40, 2001, pp. 2909-2912.

D. Gerion, W.J. Parak, S.C. Williams, D. Zanchet, C.M. Miccheel, A.P. Alivisator," Sorting Florescent Nanocrystals with DNA," J. Am. Chem. Soc., vol. 124, 2002, pp. 7070-7074.

C.J. Loweth, W.B. Caldwell, X. Peng, A.P. Alivisatos, P.G. Schultz," DNA-Based Assembly of Gold Nanocrystals," Angew. Chem. Int. Ed., vol. 38, 1999, pp. 1808-1812.

C. Mao, V.R. Thalladi, D.B. Wolfe, S. Whitesides, G.M. Whitesides, "Self-Assembled Aggregates that Spontaneously Reconfigure their Structure when their Environment Changes", J. Am. Chem. Soc., vol. 124, 2002, pp. 14508-14509.

V.M. Shelekhina, O.A. Prokhorov, P.A. Vityaz, A.P. Stupak, S.F. Gaponenko, N.V. Gaponenko, "Towards 3D Photonic Crystals", Synthetic Metals, vol. 124, 2001, pp. 137-139.

J.E.G.J. Wijnhoven, W.L. Vos, "Preparation of Photonic Crystals Made of Air Spheres in Titania", Science, vol. 281, No. 5378, Aug. 7, 1998, p. 802-804.

X. Xu, G. Friedman, K.D. Humfeld, S.A. Majetich, S.A. Asher, "Synthesis and Utilization of Monodisperse Superparamagnetic Colloidal Particles for Magnetically Controllable Photonic Crystals", Chem. Mater., vol. 14, No. 3, 2002, pp. 1249-1256.

K. Lee, S.A. Asher, "Photonic Crystal Chemical Sensors: pH and Ionic Strength", J. Am. Chem. Soc., vol. 122, No. 39, 2000, pp. 9534-9537.

J.R. Link, M.J. Sailor, "Smart Dust: Self-Assembling, Self-Orienting Photonic Crystals of Porous Si", Applied Physical Sciences, Aug. 12, 2003.

X. Xu, S.A. Majetich, S.A. Asher, "Mesoscopic Monodisperse Ferromagnetic Colloids enable Magnetically Controlled Photonic Crystals," J. Am. Chem. Soc., vol. 124, 2002, 13864-68.

C.P. Collier, T. Vossmeyer, J.R. Heath, "Nanocrystal Superlattices," Annu. Rev. Phys. Chem., vol. 49, 1998, pp. 371-404.

C.A. Mirkin, R.L. Letsinger, R.C. Mucic, J.J. Storhoff, "A DNA-Based Method for Rationally Assembling Nanoparticles into Macroscopic Materials," Letters to Nature, vol. 382, Aug. 15, 1996, pp. 607-609.

T.A. Schmedake, F. Cunin, J.R. Link, M.J. Sailor, "Standoff Detection of Chemicals using Porous Silicon "Smart Dust" Particles," Adv. Mater., vol. 14, No. 18, Sep. 16, 2002, pp. 1270-1272.

G. Vincent, "Optical Properties of Porous Silicon Superlattices," Appl. Phys. Lett., vol. 64, May 2, 1994, pp. 2367-2369.

M.P. Stewart, J.M. Buriak, "Photopatterned Hydrosilylation on Porous Silicon," Angew. Chem. Int. Ed. Engl., vol. 37, 1998, pp. 3257-3260.

R. Boukherroub, J.T.C. Wojtyk, D.D.M. Wayner, D.J. Lockwood, "Thermal Hydrosilylation of Undecylenic Acid with Porous Silicon," J. Electrochem Soc., vol. 149, 2002, pp. 59-63.

F. Cunin, T.A. Schmedake, J.R. Link, Y.Y. Li, J. Koh, S.N. Bhatia, M.J. Sailor, "Biomolecular Screening with Encoded Porous-Silicon Photonic Crystals," Nat. Mater., vol. 1, 2002, pp. 39-41.

M.G. Berger, R. Arens-Fischer, M. Thoenissen, M. Krueger, S. Billat, H. Lueth, S. Hilbrich, W. Theiss, P. Grosse, "Dielectric Filters Made of PS: Advanced Performance by Oxidation and New Layer Structures," Thin Solid Films, vol. 297, 1997, pp. 237-240.

C. Gurtner, A. W. Wun, M.J. Sailor, "Surface Modification of Porous Silicon by Electrochemical Reduction of Organo Halides," Angew. Chem. Int. Ed. Engl., vol. 38, 1999, pp. 1966-1968.

J.M. Buriak, "Organometallic Chemistry on Silicon and Germanium Surfaces," Chem. Rev., Washington, D.C., vol. 102, No. 5, 2002, pp. 1272-1308.

P.A. Snow, E.K. Squire, P.S.J. Russell, L.T. Canham, "Vapor Sensing Using the Optical Properties of Porous Silicon Bragg Mirrors," J. Appl. Phys., vol. 86, No. 4, Aug. 15, 1999, pp. 1781-1784.

T. Gao, J. Gao, M.J. Sailor, "Tuning the Response and Stability of Thin Film Mesoporous Silicon Vapor Sensors by Surface Modification," Langmuir, vol. 18, 2002, pp. 9953-9957.

H. Arwin, M. Gavutis, J. Gustafsson, M. Schultzberg, S. Zangooie, P. Tengvall, "Protein Adsorption in Thin Porous Silicon Layers," Phys. Status Sol. (a)., vol. 182, 2000, pp. 515-520.

B.E. Collins, K.P. Dancil, G. Abbi, M.J. Sailor, "Determining Protein Size Using Electrochemically Machined Pore Gradient in Silicon," Adv. Func. Mat., vol. 12, No. 3, Mar. 2002, pp. 187-191.

S. Chan, S.R. Horner, B.L. Miller, P.M. Fauchet, "Identification of Gram Negative Bacteria Using Nanoscale Silicon Microcavities," J. Am. Chem. Soc., vol. 123, 2001, pp. 11797-11798.

L.T. Canham, M.P. Stewart, J.M. Buriak, C.L. Reeves, M. Anderson, E.K. Squire, P. Allcock, P.A. Snow, "Derivatized Porous Silicon Mirrors: Implantable Optical Components with Slow Resorbability," Phys. Stat. Sol. (a)., vol. 182, 2000, pp. 521-525.

A.H. Mayne, S.C. Bayliss, P. Barr, M. Tobin, L.D. Buckberry, "Biologically Interfaced Porous Silicon Devices," Phys. Stat. Sol. (a), vol. 182, 2000, pp. 505-513.

B. Warneke, M. Last, B. Liebowitz, K.S.J. Pister, "Smart Dust: Communicating with a Cubic Millimeter Computer," IEEE Computer Society, vol. 34, No. 1, Jan. 2001, pp. 44-51.

Y.Y. Li, F. Cunin, J.R. Link, T. Gao, R.E. Betts, S.H. Reiver, V. Chin, S.N. Bhatia, M.J. Sailor, "Polymer Replicas of Photonic Porous Silicon for Sensing and Drug Delivery Applications," Science, vol. 299, Mar. 28, 2003, pp. 2045-2047.

L.T. Canham, C.L. Reeves, A. Loni, M.R. Houlton, J.P. Newey, A.J. Simons, T.I. Cox, "Calcium Phosphate Nucleation on Porous Silicon: Factors Influencing Kinetics in Acellular Simulated Body Fluids," Thin Solid Films, vol. 297, 1997, pp. 304-307.

Sailor, M.J., "Properties of Porous Silicon," The Institution of Electrical Engineers, pp. 364-370, Aug. 1997.

* cited by examiner

PHOTONIC SENSOR PARTICLES AND FABRICATION METHODS

PRIORITY CLAIM

Applicants claim priority benefits under 35 U.S.C. § 119 on the basis of Patent Application No. 60/495,436, filed Aug. 14, 2003.

STATEMENT OF GOVERNMENT INTEREST

This invention was made with Government assistance under National Science Foundation, Grant No. ECS-0088060, and Air Force Ofc. of Scientific Research, Grant No. F-49620-02-1-0288. The Government has certain rights in this invention.

TECHNICAL FIELD

A field of the invention is sensing. Example applications for particles of the invention include high throughput screening, drug discovery, biomedical implants, information display, optical switching, and chemical and biological sensor fields.

BACKGROUND ART

Microscopic devices for moving toward specific, predetermined targets to isolate and detect those targets could be invaluable for a variety of applications, such as environmental monitoring, medical diagnostic, or therapeutic applications. However, many of the components required by such microscopic devices are too small or overly complex to be fabricated using conventional lithographic tools. Manipulation of matter at a nanoscale level is accordingly highly advantageous.

Self-assembly reactions provide one route for constructing 1-, 2-, and 3-dimensional objects in this size regime. For example, covalent bonds between alkanethiols and gold substrates have been used to pattern surfaces in 2 dimensions, surface affinity properties have been used to self-assemble colloidal photonic crystals in 2 and 3 dimensions, and complementary interactions between DNA base pairs have been used to assemble nanoparticles into 3-dimensional networks. These hierarchical structures have been used for various optics and sensor applications. In general, semiconducting or metallic nanocrystals or monodisperse polymeric beads are the building blocks for this "bottom up" synthetic approach, where the structures are held together by van der Waals forces, hydrogen bonding, or other specific chemical interactions.

DISCLOSURE OF INVENTION

The invention is related to optical particles, use of optical particles in sensing applications, and methods of fabricating optical particles that can target a desired analyte. The invention is also related to the self-assembly of individual optical particles. An advantage of the invention is that it includes self-assembling individual photonic crystal sensors onto a target. In an embodiment of the invention, a processed sensor structure having two generally opposing surfaces is provided, wherein each of the opposing surfaces have different surface affinities, with a first optical structure formed on one of the opposing surfaces, and a second optical structure formed on the other of the opposing surfaces. The chemically and optically asymmetric opposing surfaces will spontaneously align at an organic liquid/water interface. Changes in the optical response of at least one of the opposing surfaces indicate the presence of a particular analyte for sensing applications.

BEST MODE FOR CARRYING OUT THE INVENTION

The invention is related to optical particles, use of optical particles in sensing applications, and methods of fabricating optical particles. It is contemplated that the chemically asymmetric optical particles have applications in high throughput screening, drug discovery, biomedical implants, information display, optical switching, and chemical and biological sensor fields. In one embodiment, a processed substrate is provided having two opposing surfaces, such as, for example, a top surface and a bottom surface, with different surface affinities and different optical signatures, with a first optical structure formed on the top surface, and a second optical structure formed on the bottom surface. While the opposing surfaces are discussed as top and bottom surfaces herein for purposes of convention, the invention contemplates use of any two opposite sides, referred to herein as oppositely.

The top and bottom surfaces are chemically and optically asymmetric. At least one of the first and the second optical structures changes its optical response when a substance in contact with the optical structure changes. For example, the top surface may be hydrophobic and the bottom surface may be hydrophilic, or vice-versa. When released from the substrate, the resulting micron-sized particle will include a hydrophobic surface and a hydrophilic surface, thereby acting as a sensor. Hence, when the sensor is placed on a liquid surface, it may automatically orient itself according to the different surface affinities with respect to the liquid. Moreover, each optical structure, one of which is disposed on either side of the sensor, may have a periodic structure on the respective surface to filter received light. For example, each optical structure is a multilayered rugate filter, wherein the rugate filters have different periodicities from one another that result in the distinct optical signatures.

The processed sensor may be fabricated from a substrate of a semiconductor or other suitable solid-state materials. Preferably, the substrate is a single-crystal material, such as a silicon (Si) crystal. In the case of the single-crystal semiconductor material, the two surfaces of the processed sensors may be processed as periodic multilayered porous surfaces known as rugate filters that diffract light of a narrow range of wavelengths. The selected wavelength is a function of the periodicity of the structure and of the refractive index of the material. When the sensor comes into contact with the target analyte, one or both of the rugate peaks will shift in a predictable manner. This spectral dependence may be used to optically sense different analytes. Thus, the invention provides optical sensors fabricated as micron-sized particles that form smart sensing dust ("smart dust") that can self align on a liquid surface for various sensing applications. The targeting behavior of the micron-sized optical sensors is effective because the sensors are removed from the substrate, and therefore exist as tiny particles that are readily capable of movement. Moreover, the aggregation of dozens or hundreds of these sensors at the target provides useful signal amplification.

Methods for fabricating optical particles, such as the micron-sized sensors, preferably include an electrochemical etching process, which is a relatively quick and inexpensive process, to produces chemically modified particles. For example, one embodiment of this process includes a semiconductor structure, such as a Si structure, that is produced by electrochemically etching silicon with application of a time-varying electrical current so that the etched part of the silicon structure becomes porous. Next, the etched silicon structure is modified by a thermal, photochemical, or electrochemical process to exhibit a desired property, e.g., being hydrophobic or hydrophilic. Thus, the two processing steps of etching and modification may be repeated on the same substrate to generate the desired structures, which are dual sided particles wherein each side includes a unique surface affinity.

Figure 1:
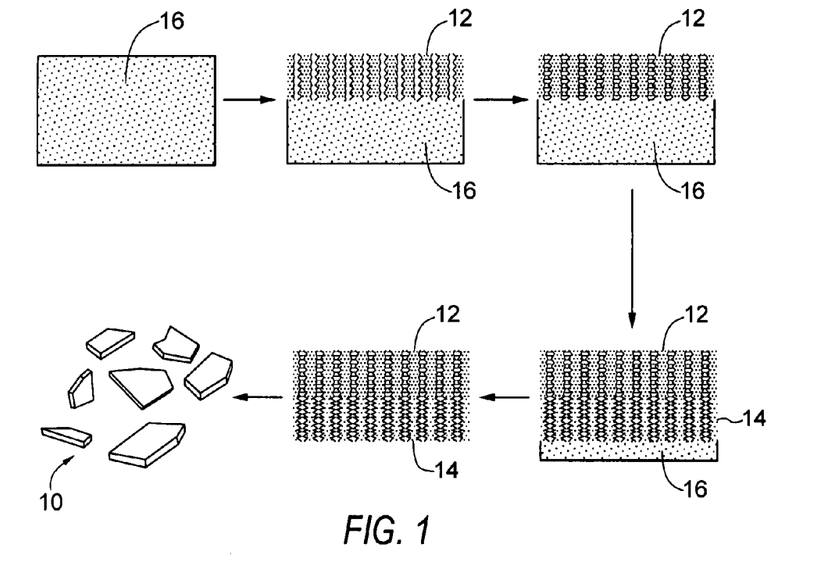
FIG. 1 is a schematic diagram illustrating the synthesis of dual-sided photonic crystals according to a preferred embodiment of the invention.

Turning now to FIG. 1, a preferred embodiment of the instant invention is directed to the synthesis and use of photonic crystals of porous silicon (Si) that spontaneously assemble and orient, and are capable of sensing the local environment and reporting same macroscopically. The photonic crystals, designated generally at 10, are generated by electrochemically etching at least two discrete porous multilayered dielectric mirrors 12, 14 into a silicon substrate 16, one on top of the other. A first optical structure 12, which is preferably as a dielectric mirror, such as a Rugate filter, is etched on the silicon substrate 16, and is then modified prior to etching of the second optical structure 14, which is subsequently prepared to have an optical reflectivity spectrum that is distinct from the first optical structure. Modification of the first optical structure 12 is preferably thermal hydrosilylation with, for example, dodecene. However, it is contemplated that other agents for thermal hydrosilylation would likewise render a hydrophobic surface.

Following etching of both the first and second optical structures 12, 14 on the silicon substrate 16, a film, indicated generally at 18, that includes the first and second structures is removed from the silicon substrate. The second structure 14 is then selectively modified by one of a plurality of methods to obtain a structure having a different periodicity and different surface chemistry than the first structure 12. For example, the second structure 14 may be oxidized to impart a hydrophilic character to the second structure, while the first structure 12 retains its hydrophobic character. However, it is contemplated that other oxidizing agents would likewise render a hydrophilic surface. The film 18 is then fractured into small particles, resulting in chemically asymmetric particles 10 that will spontaneously align at an organic liquid/water interface, with a hydrophobic side oriented toward the organic phase and the hydrophilic side toward the water. Fracture may proceed via one of a plurality of mechanisms such as sonication or mechanical agitation. Preferably, however, the film 18 is subjected to sonication to fracture the film into micron-sized particles 10. The micron-sized particles 10 may then be used as micron-sized sensors.

The micron-sized photonic particles 10 resulting from fabrication in this manner are useful in a vast array of applications, ranging from environmental monitoring, medical diagnostic, therapeutic applications, high throughput screening, drug discovery, biomedical implants, information display, optical switching, taggants and tracers to be used in forensics, and chemical and biological sensor fields.

For exemplary purposes, one embodiment of an exemplary sensing application is provided. A predetermined receptor for a target molecule may be chemically bound to one side of the dual-sided sensors. The receptor will chemically bind, or have an affinity for, the target cell or analyte, causing all of the sensors to self-assemble at the surface and self-align with the receptor-modified surface facing the target analyte. The second surface would be modified to have a general affinity for the medium in which the analysis is conducted. For example, the second surface may be modified to have an affinity for the human body or for water. Aggregation of the sensors at the target and changes in the optical properties of the rugate filters would signal the location and detection of the desired target analyte.

Materials and Methods

A particular embodiment method to produce self-assembling and self-organizing bifunctional particles of porous silicon photonic crystals follows the process described with respect to FIG. 1, and has been used to produce prototype particles of the invention. A multilayered porous Si dielectric mirror is first electrochemically etched into the single-crystal Si (100) substrate (degenerate p-type, B doped, <1 mΩ-cm resistivity, obtained from Siltronix, Inc.). The etching solution consists of a 1:3 by volume mixture of absolute ethanol (Aldrich Chemicals) and aqueous 49% HF (Quantum Chemicals). Etching is carried out in a Teflon cell using a two-electrode configuration with a Pt mesh counter electrode. A sinusoidal current density waveform varying between 11.5 and 34.6 mA/cm$^2$ is applied for 100 cycles and a periodicity of 7 s. This side of the porous mirror is then thermally hydrosilylated with 1-dodecene to obtain a chemically stable hydrophobic mirror. The second mirror having a different periodicity than the first mirror is then etched into the substrate, immediately beneath the first, by placing the sample back in the Teflon etch cell and applying a sinusoidal current density varying between 11.5 and 34.6 mA/cm$^2$, with 100 repeats and a periodicity of 8.7 s. The entire structure is then removed from the Si substrate by application of a current density pulse of 15.4 mA/cm$^2$ for 45 s in an ethanol solution that is 3.3% by weight aqueous HF. The freestanding film is then placed in an oven in air at 100° C. for 15 h. This step preferentially produces a thermal oxide on the more reactive, hydrogen-terminated freshly etched layer, imparting a hydrophilic character to the second mirror while the hydrosilylated side retains its hydrophobic nature, as determined by contact angle measurements (advancing contact angle with water, hydrophobic side: 92°; hydrophilic side: 39°). The chemical nature of the two faces is confirmed by diffuse reflectance infrared spectroscopy; absorption bands characteristic of aliphatic C—H vibrational modes (2960-2850 and 1470 cm$^{-1}$) are observed from the hydrosilylated side and a prominent band assigned to Si—O stretching (1054 cm$^{-1}$) is observed after oxidation. The film is broken into micron-sized particles by ultrasonication as previously described.

Results and Discussion

Figure 2:
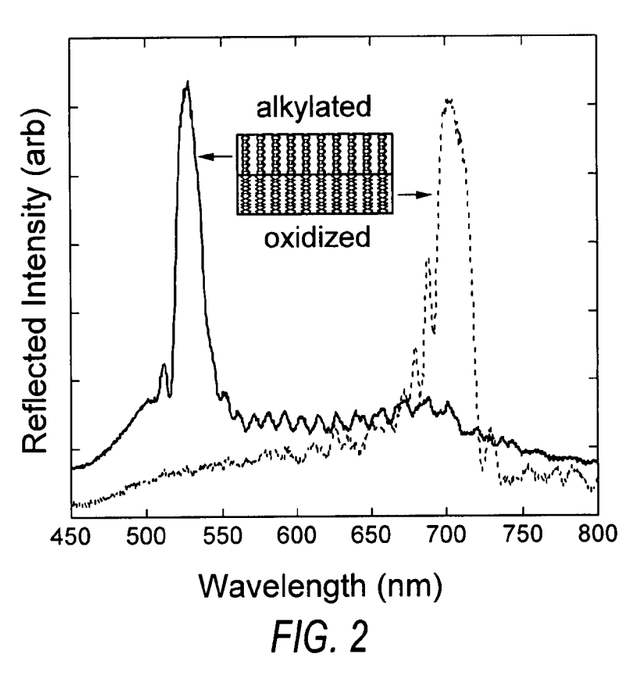
FIG. 2 is a graph illustrating the reflectivity spectrum taken from each side of a bifunctional porous Si rugate sensor.

Porous Si prepared using a sinusoidal current density waveform possesses an approximately sinusoidal porosity gradient in the direction of pore propagation. The porosity gradient results in a periodic variation in refractive index in the film. This structure, generally referred to as a rugate filter, produces a sharp diffraction feature in the optical reflectivity spectrum of the film, as illustrated in FIG. 2. When prepared, the hydrophobic side of the sensor is typically green (shown as solid), whereas the hydrophilic side is typically red (shown as dashed). The wavelength of the reflectivity maximum is determined by the periodicity and amplitude of the current waveform used in the etch.

As illustrated in FIG. 2, the two traces indicate each side of the film dry, where the solid line represents reflected intensity obtained from the side of the film that contained a mirror etched using a sinusoidal current varying between 11.5 and 34.6 mA/cm$^2$. This side of the porous mirror was then hydrosilylated with 1-dodecene. The dashed line is obtained from the side of the film that contained the second mirror, etched using a sinusoidal current varying between 11.5 and 34.6 mA/cm$^2$ and then removed from the Si substrate. This side of the porous mirror was then thermally oxidized. The total thickness of the porous Si film is approximately 100 µm.

The tandem etch/modify method provides a general means for producing optical films with spatially resolved, chemically distinct layers. The main requirement of the chemical modification reactions is that they be stable to the hydrofluoric acid etchant used in generating subsequent porous Si layers. It is anticipated that a number of chemical and electrochemical modification strategies developed for porous Si can be used with this procedure.

The bifunctional films will spontaneously orient at the surface of water, with the hydrophobic side facing up. If a small (about 2 mm on an edge) piece of the film floating on a water surface is picked up with forceps and flipped over, it will spontaneously right itself. The phenomenon is easily observed with the unaided eye due to the significant color difference between the hydrophobic and hydrophilic mirrors (green vs red, respectively, for example). The addition of a hydrophobic liquid that is immiscible with water (such as heptane) to the water layer causes the films to localize at the liquid/liquid interface, with the hydrophobic mirror facing the hydrophobic liquid phase.

Figure 3:
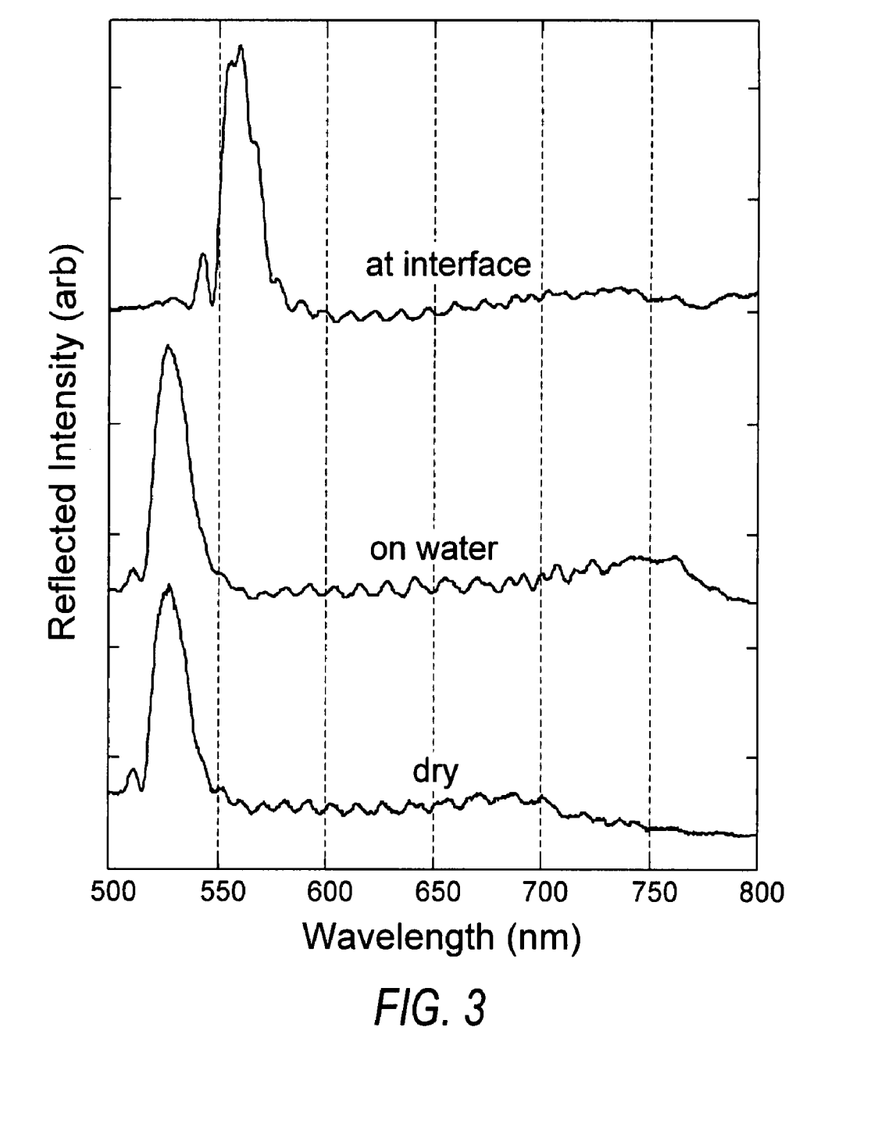
FIG. 3 is a graphic illustrating the reflectivity spectra of a hydrophobic surface of a bifunctional porous Si film illustrated in FIG. 2.

The reflectivity spectrum from the bifunctional mirrors provides a signal that reports on the interfacial interaction. The position of the spectral peaks in porous Si dielectric mirrors is a strong function of the average refractive index of the layers, and shifts in the photonic features have been shown to provide a very sensitive transduction modality for sensing of condensable vapors, proteins, DNA, and other molecules that can enter the pores. Turning now to FIG. 3 for exemplary purposes only, in one embodiment, the hydrosilylated layer is designed to display a spectral wavelength maximum of 530 nm in air, as illustrated in the "dry" trace, which is the same data represented by the solid line of FIG. 2 and obtained with the sample in air. Liquid water will not infiltrate the hydrophobic pores, and the peak displays no discernable shift when the film is in contact with water, as illustrated in the "on water" trace of FIG. 3, which represents the spectrum of the hydrophobic side of the sample when it is floating on water. By contrast, in the presence of the heptane phase, the spectral feature shifts to 560 nm, as illustrated in the "at interface" trace of FIG. 3, which represents the spectrum of the sample sitting at the water/heptane interface.

Figure 4:
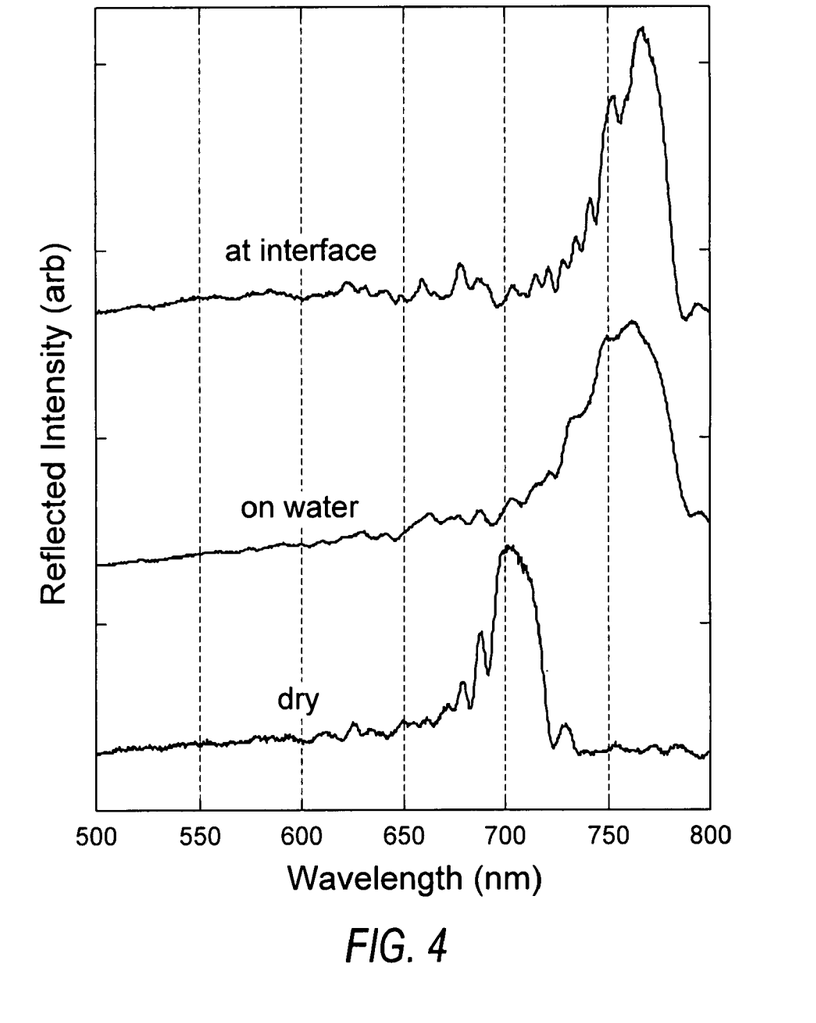
FIG. 4 is a graph illustrating the reflectivity spectra of the hydrophilic surface of the bifunctional porous Si film illustrated in FIG. 2.

Turning now to FIG. 4, the complementary effect is observed on the opposite side of the film. In one exemplary embodiment, the hydrophilic mirror displays a wavelength maximum of 702 nm (FIG. 4, "dry"); in contact with water the main spectral feature shifts to 762 nm (FIG. 4, "on water"). Subsequent addition of heptane to form the two phase mixture does not significantly shift this peak (to 767 nm, FIG. 4, "at interface").

The same optical effects are observed on smaller, which we refer to as "smart dust" particles, and which are made by fracture of the prepared porous Si films, for example through ultrasonication. The particles are observed to spontaneously assemble and orient at the interface of a small drop of dichloromethane in water. Spectra similar to those observed with the larger (mm-size) films (FIGS. 3 and 4) are observed on the micron-size particles as well, confirming that self-orientation and self-assembly occurs with the small particles. In this case it is very difficult to measure the reflectivity spectrum from an individual particle, but quite simple to measure the spectrum from an ensemble of the particles once they have assembled and oriented at the interface. The targeted assembly process thus provides an important amplification function.

The chemically asymmetric "smart dust" particles enable interesting applications in high throughput screening, drug discovery, biomedical implants, information display, optical switching, and chemical and biological sensor fields. Use of the chemically stratified materials as a self-assembling chemical sensor is anticipated. The chemically asymmetric particles spontaneously target and align themselves at an organic liquid/water interface with the hydrophobic side oriented toward the organic phase and the hydrophilic side toward the water. A characteristic shift in the optical spectra of both optical structures signals the arrival of the particle at the interface. With the appropriate recognition elements, these self-targeting and self-orienting materials may be applied to a variety of interesting problems. More specifically, the predetermined receptor for a target analyte may be chemically bound to one side of the dual-sided sensor of the instant invention, thereby causing the sensor to chemically bind or have an affinity for the target cell or target analyte. Possible recognition elements that could be incorporated into this method include homing peptides, antibodies, sugars, DNA or RNA strands, enzyme inhibitors, membrane-bound proteins, and other biological recognition elements. Thus, the sensors would self-align and self-assemble at the surface of the target cell or target analyte, with the receptor-modified surface facing the target cell or target analyte. For example, the particles might be used to locate, identify, and/or destroy certain cell types in the body or they might be used to locate and identify pathogenic bacteria in food or drinking water. Several features of porous Si are useful in this regard, for example, porous Si has been shown to be biocompatible and it is currently under active investigation as a component in resorbable drug delivery systems. Additionally, the photonic features from the multilayers can be observed at a distance or through human tissue, and the porous layers can act as a sensitive biosensor for proteins or DNA.

Still other embodiments of the invention provide methods useful for optoelectronics applications, such as optical switching or information display. Preparation of photonic crystal allow tuning of the rheological properties (such as hydrophobicity/hydrophilicity), and also allows the construction of a designed porous material with differing surface affinities. It is contemplated that these characteristics may be useful for drug delivery applications as well, especially where the porous Si material (or a derivative of it) is used to deliver one or more drugs at controlled or predetermined rates. By using this method (etching followed by chemical modification), one can prepare a host material for a drug or drugs that would allow one to tune the rate at which the drug is released. Normally drugs are released in the body based on the dissolution rate of the material (such as with an aspirin tablet in the stomach). Since the pore size and nature of the surface can be changed in the film with each step, it is contemplated that, for instance, a drug could be provided in one layer that is released over a period of two weeks, while a different drug provided in a different layer is released over a period of hours. Release profile can be tuned in this fashion, as well, so that instead of a steadily decaying concentration of drug, one drug may exhibit an initial increase in concentration followed by a decrease, or a more sustained (constant) concentration can be maintained.

While various embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the following claims.

What is claimed is:

1. A method of fabricating photonic crystals of porous material, comprising:
   providing a silicon substrate;
   etching the silicon substrate to obtain a first patterned layer;
   treating the first dielectric mirror to impart a first surface affinity to the first patterned layer;
   etching a second patterned layer immediately beneath the first patterned layer to a second patterned layer, wherein the first and second patterned layers are patterned to produce a characterstic reflection and predetermined wavelengths;
   releasing the first and second patterned layers as a freestanding film;
   treating the second patterned layer to impart a second surface affinity to the second patterned layer; and
   fracturing the free standing film into micron-sized particles.

2. The method of claim 1 wherein the silicon substrate comprises a single crystal silicon substrate.

3. The method of claim 1 wherein the first patterned layer is treated to impart a hydrophobic character.

4. The method of claim 1 wherein the second dielectric mirror is treated to impart a hydrophilic character.

5. The method of claim 1 further comprising hydrosilylating the first patterned layer to impart a hydrophobic character.

6. The method of claim 1 further comprising oxidizing the second patterned layer to impart a hydrophilic character.

7. The method of claim 1 wherein said etching comprises etching the silicon substrate with a time-varying electrical current to obtain the first patterned layer.

8. The method of claim 7 wherein said etching comprises etching the silicon substrate with a time-varying electrical current to obtain the second patterned layer.

9. The method of claim 1 wherein said releasing comprises applying a current pulse to release the first and second patterned layers as a freestanding film.

10. The method of claim 1 wherein said fracturing comprises ultrasonication of the freestanding film to fracture the freestanding film.

11. The method of claim 1 wherein said etching comprises etching the first patterned layer to have a first periodicity and the second patterned layer to have a second periodicity that is different from the first periodicity.

12. The method of claim 11 wherein said etching comprises etching first and second rugate filters on the silicon substrate.

13. Photonic crystal particles (10) of porous silicon that spontaneously assemble and orient to sense a local environment comprising:
   a first patterned layer (12) having hydrophobic properties; and
   a second patterned layer (14) disposed oppositely said first patterned layer, said second patterned layer having hydrophilic properties.

14. The particles of claim 13 wherein said first and second patterned layers comprise first and second rugate filters, respectively.

15. The particles of claim 13 wherein said first patterned layer has a first periodicity and said second patterned layer has a second periodicity that is different from said first periodicity.

16. A sensing system of photomc crystal particles (10) of porous silicon that spontaneously assemble and orient to sense a local environment comprising:
   an aqueous environment suspected of including a target analyte;
   a plurality of fractured silicon particles (10) having a first surface (12) that will self-align with the target analyte and a second surface (14) that will self-align with the aqueous environment.

17. The sensing system of claim 16 wherein said first surface includes a first rugate filter and said second surface includes a second rugate filter.

18. The sensing system of claim 16 wherein said first surface is hydrophobic and said second surface is hydrophilic.

19. The sensing system of claim 16 wherein said aqueous environment is water.

20. The sensing system of claim 16 where the target analyte is hydrophobic.

21. A method of sensing a target analyte in solution comprising:
   etching at least first and second rugate filters (12, 14) on a silicon substrate, with the first and second rugate filters being disposed one on top of the other;
   varying surface affinities of the first and second rugate filters such that one of the first and second rugate filters exhibits hydrophilicity and the other exhibits hydrophobicity;
   removing the silicon substrate;
   fracturing a film comprising the first and second rugate filters to obtain particles having a hydrophobic side and a hydrophilic side;
   immersing the particles in an aqueous environment suspected of containing the target analyte; and
   observing the optical characteristics of the particles.

22. The method of claim 21 wherein said varying comprises attaching dodecene to the first rugate filter to obtain the hydrophobic side and attaching an oxide species to obtain the hydrophilic side.

23. The method of claim 21 wherein said observing comprises observing changes in optical reflectivity properties of the particles.

* * * * *

UNITED STATES PATENT AND TRADEMARK OFFICE
CERTIFICATE OF CORRECTION

PATENT NO. : 7,318,903 B2
APPLICATION NO. : 10/567917
DATED : January 15, 2008
INVENTOR(S) : Jamie R. Link and Michael J. Sailor It is certified that error appears in the above-identified patent and that said Letters Patent is hereby corrected as shown below:

| | | |
|---|---|---|
| Claim 1 | Col. 7, line 26 | Please delete "silicon" |
| | Col. 7, line 27 | Please delete "silicon" |
| | Col. 7, line 29 | Please delete "dielectric mirror" and insert --patterned layer-- therefor |
| | Col. 7, line 32 | Please delete "to a second patterned layer" |
| Claim 2 | Col. 7, line 42 | Please delete "silicon" |
| Claim 4 | Col. 7, line 46 | Please delete "dielectric" and insert --patterned-- therefor |
| | Col. 7, line 47 | Please delete "mirror" and insert --layer-- therefor |
| Claim 7 | Col. 7, line 54 | Please delete "silicon" |
| Claim 8 | Col. 7, line 57 | Please delete "silicon" |
| Claim 12 | Col. 8, line 4 | Please delete "silicon" |
| Claim 13 | Col. 8, line 6 | Please delete "(10) of porous silicon" and insert --of porous material-- therefor |
| | Col. 8, line 9 | Please delete "(12)" |
| | Col. 8, line 11 | Please delete "(14)" |
| Claim 16 | Col. 8, line 21 | Please delete "(10)" |
| | Col. 8, line 22 | Please delete "silicon" and insert --material-- therefor |
| | Col. 8, line 27 | Please delete "silicon particles (10)" and insert --particles-- therefor |
| | Col. 8, line 28 | Please delete "(12)" |
| | Col. 8, line 29 | Please delete "(14)" |

UNITED STATES PATENT AND TRADEMARK OFFICE
CERTIFICATE OF CORRECTION

PATENT NO. : 7,318,903 B2
APPLICATION NO. : 10/567917
DATED : January 15, 2008
INVENTOR(S) : Jamie R. Link and Michael J. Sailor It is certified that error appears in the above-identified patent and that said Letters Patent is hereby corrected as shown below:

Claim 21  Col. 8, line 43   Please delete "(12,14)"
             Col. 8, line 44   Please delete "silicon"
             Col. 8, line 50   Please delete "silicon"

Signed and Sealed this

Seventeenth Day of June, 2008

JON W. DUDAS
*Director of the United States Patent and Trademark Office*